United States Patent [19]

Oxenbøll et al.

[11] Patent Number: 5,741,688
[45] Date of Patent: Apr. 21, 1998

[54] ALKALINE GLUCOSE OXIDASE OBTAINED FROM CLADOSPORIUM OXYSPORUM

[75] Inventors: Karen M. Oxenbøll; Joan Qi Si; Jesper Aagaard, all of Bagsvaerd, Denmark

[73] Assignee: Novo Nordisk A/S, Bagsvaerd, Denmark

[21] Appl. No.: 446,645

[22] PCT Filed: May 3, 1995

[86] PCT No.: PCT/DK95/00178

§ 371 Date: May 25, 1995

§ 102(e) Date: May 25, 1995

[87] PCT Pub. No.: WO95/29996

PCT Pub. Date: Nov. 9, 1995

[30] Foreign Application Priority Data

May 3, 1994 [DK] Denmark ................................. 504/94

[51] Int. Cl.$^6$ ................................. C12N 9/04; A23B 5/00
[52] U.S. Cl. ................................. 435/190; 426/10; 426/20; 426/28; 426/61
[58] Field of Search ................................. 435/190; 426/10, 426/20, 28, 61

[56] References Cited

U.S. PATENT DOCUMENTS

| 4,045,296 | 8/1977 | Sternberg ................................. 435/11 |
| 4,990,343 | 2/1991 | Haamsilta et al. ................................. 426/10 |
| 5,288,746 | 2/1994 | Pramod ................................. 252/95 |

FOREIGN PATENT DOCUMENTS 0 338 452  10/1989  European Pat. Off. .

OTHER PUBLICATIONS

Moore–Landecker, E. Fundamentals of the fungi p. 262, 1982.
Oji Paper Co., JP 6141854, Dialog Abs. No. 009937307 (1994).
Arica et al. J. Chem. Technol. Biotechnol. vol. 58(3) pp. 287–292. Abstract Enclosed.

*Primary Examiner*—Leon B. Lankford, Jr.
*Assistant Examiner*—Christopher R. Tafe
*Attorney, Agent, or Firm*—Steve T. Zelson, Esq.; Cheryl H. Agris, Esq.

[57] ABSTRACT

A glucose oxidase obtained from a *Cladosporium oxysporum* strain, designated as CBS 163.94, characterized by a pH-optimum in he range pH 6–7, having more than 75% of maximum activity at pH 8, determined at 30° C. with D-glucose as substrate.

4 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( x i ) SEQUENCE DESCRIPTION: SEQ ID NO:1:

Ala Ser Pro Ala Glu Pro Pro Val Val Ala Ala
1               5                      1 0

ALKALINE GLUCOSE OXIDASE OBTAINED FROM CLADOSPORIUM OXYSPORUM

CROSS-REFERENCE TO RELATED APPLICATIONS

This application is a continuation of PCT/DK95/00178 filed May 3, 1995, which is incorporated herein by reference.

FIELD OF INVENTION

The present invention relates to a novel glucose oxidase, to a process for its production and to its use in bleaching and detergent compositions, as well as to its use as a dough strengthener.

BACKGROUND OF THE INVENTION

Glucose oxidases are enzymes that catalyze the oxidation of glucose with oxygen whereby hydrogen peroxide is formed. Such enzymes are known from microbial, plant and animal origins, e.g., glucose oxidase from Aspergillus, Penicillium and Talaromyces. Glucose oxidase has been described as useful for various purposes, e.g., for bleaching purposes and in the baking industry, useful for strengthening the dough.

An example of a commercial glucose oxidase is Gluzyme™, an *Aspergillus niger* glucose oxidase, available from Novo Nordisk A/S. This and similar products from other commercial sources have an acidic pH optimum, typically around pH 5, which means that they are not very active in detergent solutions due to the alkaline character of the detergents.

It is an object of the present invention to provide novel glucose oxidases with improved performance in neutral and alkaline solutions.

SUMMARY OF THE INVENTION

In this invention it is surprisingly found that a glucose oxidase with a neutral pH optimum may be produced from strains of Cladosporium.

Accordingly, the present invention relates to a glucose oxidase characterized by a pH-optimum in the range pH 6–7, having more than 75% of maximum activity at pH 8, determined at 30° C. with D-glucose as substrate.

BRIEF DESCRIPTION OF DRAWINGS

The present invention is further illustrated by reference to the accompanying drawings, in which.

□: a dough with no added conditioner (=reference)

▽: a dough containing 20 ppm $KBrO_3$.

◇: a dough containing 500 UNITS per kg of flour of a glucose oxidase from *A. niger*.

Δ: a dough containing 500 UNITS per kg of flour of a glucose oxidase of the invention, obtained as described in Example 1.

Figure 3:
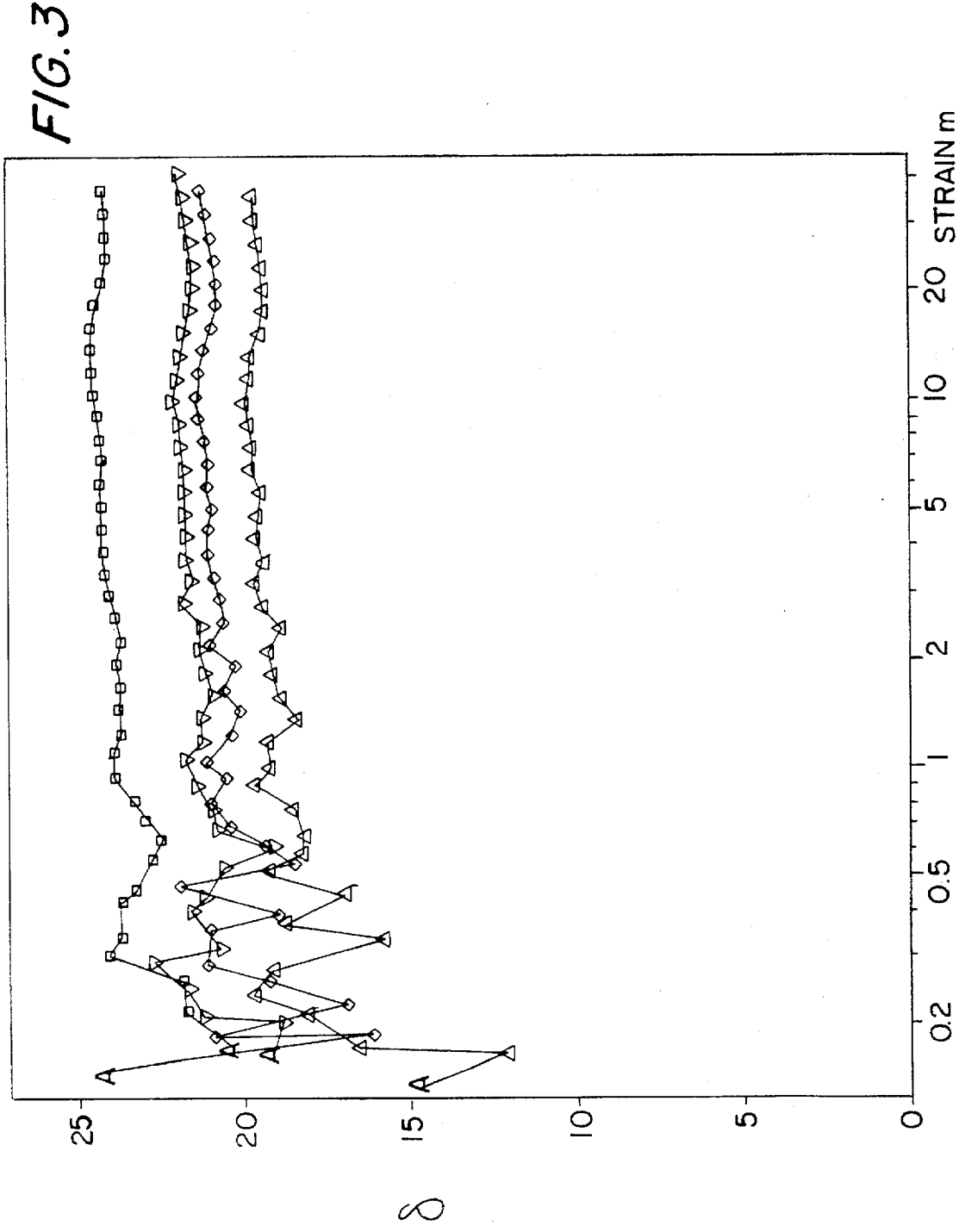

FIG. 3 shows the viscoelastic phase angle δ in gluten from 4 different doughs characterized with the following symbols:

□: a dough with no added conditioner (=reference)

▽: a dough containing 20 ppm $KBrO_3$.

◇: a dough containing 500 UNITS per kg of flour of a glucose oxidase from *A. niger*.

Δ: a dough containing 500 UNITS per kg of flour of a glucose oxidase of the invention, obtained as described in Example 1.

DETAILED DESCRIPTION OF THE INVENTION

Microorganism

According to the invention, glucose oxidase is obtainable from a glucose oxidase producing strain of Cladosporium, preferably *Cladosporium oxysporum*.

The genus Cladosporium is characterized primarily by the formation of conidia in branching chains, which are very fragile and readily break up into units. The conidia can be either hyaline or pigmented, smooth or roughened, continuous or septate. The conidiophores are erect and pigmented, branching irregularly at the apex. *Cladosporium oxysporum* is further described by M. B. Ellis in *Dermatiaceous Hyphomycetes*, 1971, p. 312, CAB International, UK.

A strain representative of *Cladosporium oxysporum* has been deposited according to the Budapest Treaty on the International Recognition of the Deposits of Microorganisms for the Purpose of Patent Procedures, on 25 Mar. 1994, at Centraal-bureau voor Schimmelcultures (CBS), under Accession No. CBS 163.94.

Production of Glucose Oxidase

Glucose oxidase of the invention may be produced by aerobic cultivation of the above mentioned microbial strain on a nutrient medium containing suitable carbon and nitrogen sources, such media being known in the art. A temperature in the range of from 20° C. to 30° C. is suitable for growth and glucose oxidase production.

Alternatively, glucose oxidase of the invention can be produced by aerobic cultivation of a transformed host organism containing the appropriate genetic information from the above mentioned strain. Such transformants can be prepared and cultivated by methods known in the art:

Cloning a DNA Sequence Encoding a Glucose Oxidase

The DNA sequence encoding a glucose oxidase of the invention may be isolated from any cell or microorganism producing the glucose oxidase in question, using various methods well known in the art. First, a genomic DNA and/or cDNA library should be constructed using chromosomal DNA or messenger RNA from the organism that produces the glucose oxidase to be studied. Then, if the amino acid sequence of the glucose oxidase is known, homologous, labelled oligonucleotide probes may be synthesized and used to identify glucose oxidase-encoding clones from a genomic library prepared from the organism in question. Alternatively, a labelled oligonucleotide probe containing sequences homologous to a known glucose oxidase gene could be used as a probe to identify glucose oxidase-encoding clones, using hybridization and washing conditions of lower stringency. According to the present invention preferred probes may be constructed on the basis of SEQ ID No. 1.

Yet another method for identifying glucose oxidase-encoding clones would involve inserting fragments of genomic DNA into an expression vector, such as a plasmid, transforming glucose oxidase-negative bacteria with the resulting genomic DNA library, and then plating the transformed bacteria onto agar containing a substrate for glucose oxidase thereby allowing clones expressing the glucose oxidase to be identified.

Alternatively, the DNA sequence encoding the enzyme may be prepared synthetically by established standard methods, e.g. the phosphoamidite method described by S. L. Beaucage and M. H. Caruthers in *Tetrahedron Letters* 22, 1981, pp. 1859–1869 or the method described by Matthes et al. in *The EMBO J.* 3, 1984, pp. 801–805. In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. in *Science* 239, 1988, pp. 487–491.

Expression of Glucose Oxidase

According to the invention, a glucose oxidase-encoding DNA sequence produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a glucose oxidase of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a glucose oxidase of the invention, especially in a bacterial host, are the promoter of the lac operon of *E.coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyO), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in leukaryotes, polyadenylation sequences operably connected to the DNA sequence encoding the glucose oxidase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular.

Procedures suitable for constructing vectors of the invention encoding a glucose oxidase and containing the promoter, terminator and other elements, respectively, are well known to persons skilled in the art (cf., for instance, Sambrook et al. in *Molecular Cloning: A Laboratory Manual*, 2nd Ed., Cold Spring Harbor, 1989).

The cell of the invention, either comprising a DNA construct or an expression vector of the invention as defined above, is advantageously used as a host cell in the recombinant production of a glucose oxidase of the invention. The cell may be transformed with the DNA construct of the invention encoding the glucose oxidase conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E.coli*.

The transformation of the bacteria may, for instance, be effected by protoplast transformation or by using competent cells in a manner known per se.

The yeast organism may favourably be selected from a species of Saccharomyces or Schizosaccharomyces, e.g., *Saccharomyces cerevisiae*. The filamentous fungus may advantageously belong to a species of Aspergillus, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a glucose oxidase of the invention, which method comprises cultivating a host cell as described above under conditions conducive to the production of the glucose oxidase and recovering the glucose oxidase from the cells and/or culture medium.

The medium used to cultivate the cells may be any conventional medium suitable for growing the host cell in question and obtaining expression of the glucose oxidase of the invention. Suitable media are available from commercial suppliers or may be prepared according to published recipes (e.g., as described in catalogues of the American Type Culture Collection).

The glucose oxidase secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Assay for Glucose Oxidase Activity

Glucose oxidase activity is determined in the following way: Glucose oxidase oxidizes D-glucose in the presence of oxygen producing hydrogen peroxide. The hydrogen peroxide formed, in the presence of peroxidase, oxidizes ABTS (2,2'-azinobis(3-ethylbenzothiazoline-6-sulfonate)). The greenish-blue colour resulting after a fixed reaction time measured as the absorbance at 418 nm is a function of the amount of hydrogen peroxide. In the assay the following concentrations, pH, temperature and reaction time are used: D-glucose: 100 mM; ABTS: 0.4 mM; phosphate buffer: 100 mM; pH: 7.0; temperature: 30° C.; reaction time: 20 min. The activity of glucose oxidase is given in UNITS (1 UNIT is the amount of glucose oxidase which under the above standard conditions forms 1 µmole of hydrogen peroxide per minute).

Physico-chemical Properties of the Glucose Oxidase

Figure 1:
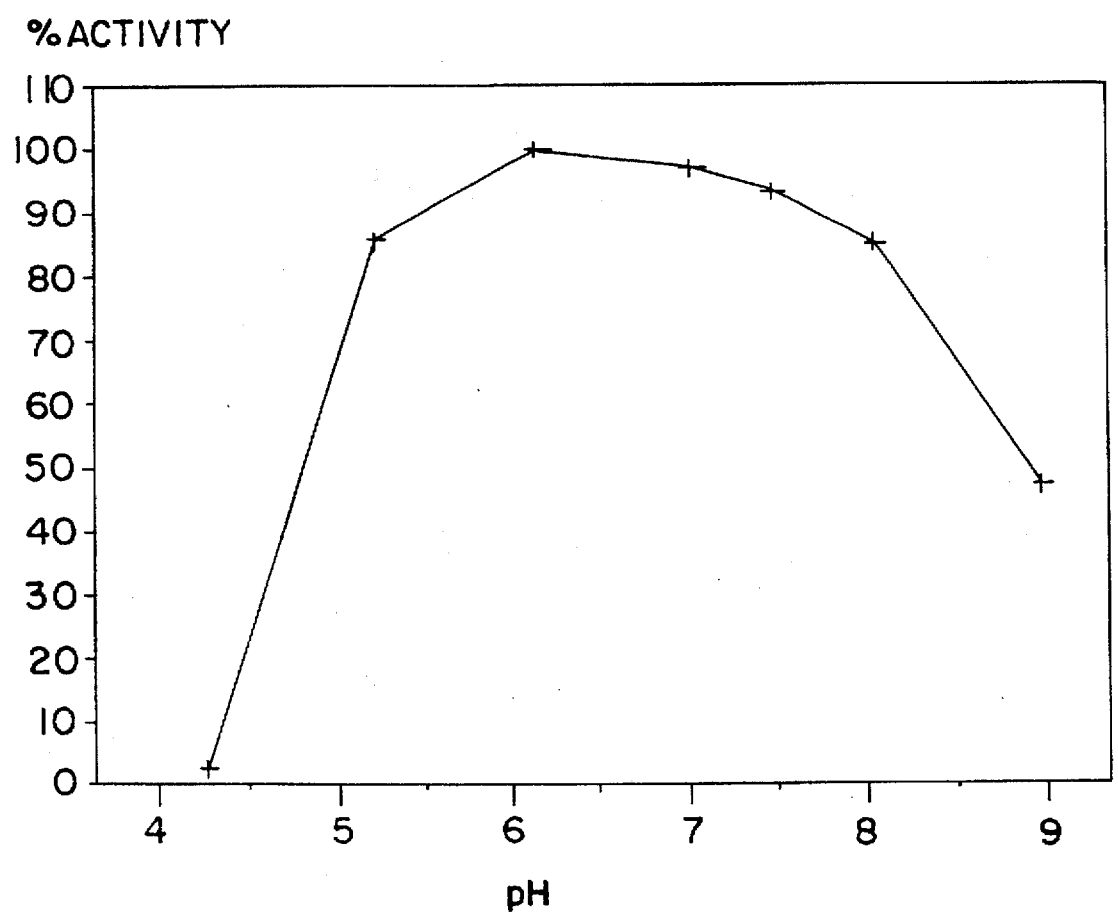
FIG. 1 shows the relation between pH and the glucose oxidase activity of a novel glucose oxidase according to the invention (the glucose oxidase obtained according to Example 1), with D-glucose as substrate in the presence of oxygen at 30° C., using a buffer system adjusted to predetermined pH values of from pH 4 to pH 9.

The glucose oxidase of the invention (obtained according to Example 1) possesses the following property:

A pH profile as shown in FIG. 1, which was determined at 30° C. in the pH range of from pH 4 to pH 9. The assay for glucose oxidase activity described above was run in a buffer of $CH_3COOH$, $KH_2PO_4$ and $H_3BO_3$ at a glucose level of 100 mM. The reaction time was 20 minutes. The peroxidase reaction was run separately after the incubation of the glucose oxidase. It appears from FIG. 1 that the enzyme possesses glucose oxidase activity from approximately pH 4 to above pH 9, having optimum in the range pH 6–7, and more than 75% of maximum activity at pH 8.

N-terminal.

An amino acid sequence of an enzyme may be determined using standard methods for obtaining and sequencing peptides, for example as described by Findlay & Geisow (Eds.), *Protein Sequencing—a Practical Approach*, 1989, IRL Press.

The N-terminal amino acid sequence of the glucose oxidase obtained from *Cladosporium oxysporum*, CBS 163.94, fermented and purified as described in Example 1, was found to be:

Ala-Ser-Pro-Ala-Glu-Pro-Pro-Val-Val-Ala-Ala (SEQ ID No. 1).

A peptide is considered to be X% homologous to the parent glucose oxidase if a comparison of the respective amino acid sequences, performed via known algorithms, such as the one described by Lipman and Pearson in *Science* 227, 1985, p. 1435, reveals an identity of X%.

The present invention relates to a glucose oxidase comprising an N-terminal amino acid sequence identical to that shown in SEQ ID No. 1 or a glucose oxidase being at least 70% homologous with SEQ ID No.1 in the N-terminal, preferably being at least 80% homologous with SEQ ID No.1 in the N-terminal, more preferably being at least 90% homologous with SEQ ID No. 1.

Immunochemical Properties

The immunochemical properties can be determined immunologically by cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques; Blackwell Scientific Publications (1983), Chapters 5 and 14. The terms "antigenic identity" and "partial antigenic identity" are described in the same book, Chapters 5, 19 and 20.

Monospecific antiserum may be generated according to the above mentioned method by immunizing rabbits with a glucose oxidase of the invention. The immunogen is mixed with Freund's adjuvant and injected subcutaneously into rabbits every second week. Antiserum is obtained after a total immunization period of 8 weeks, and immunoglobulin prepared therefrom as described by N. H. Axelsen. supra.

According to the invention a glucose oxidase displaying immunochemical cross-reactivity with an antibody raised against a glucose oxidase obtainable from a strain of the genus Cladosporium is preferred, in particular a glucose oxidase having immunochemical properties identical to those of a glucose oxidase obtainable from a strain of the genus Cladosporium.

Industrial Applications

The glucose oxidase of the invention possesses valuable properties allowing for various industrial applications. In particular the enzyme, in having activity in the alkaline region, finds potential application in washing detergent compositions as a hydrogen peroxide source, used alone or preferably together with a peroxidase, more preferably used together with a peroxidase and an oxidizable substrate such as an organic compound, such as a phenolic compound, e.g., p-hydroxybenzenesulfonate, or one of the compounds disclosed in WO 94/12621.

The enzyme may also be very useful in the baking industry due to its excellent ability for improving the properties of doughs/breads (for documentation see Example 2+3).

The enzyme also has many potential applications in the personal care area, for example in personal care products such as tooth paste, mouthwash, denture cleaner, liquid soap, skin care creams and lotions, hair care and body care formulations, and solutions for cleaning contact lenses. In particular the glucose oxidase of the invention may be very useful in tooth paste, alone or together with other enzymes, preferably together with an amyloglucosidase and a lactoperoxidase as such a combination of enzymes forms a very efficient antibacterial system:

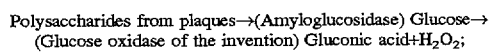
Polysaccharides from plaques→(Amyloglucosidase) Glucose→
(Glucose oxidase of the invention) Gluconic acid+$H_2O_2$;

the formed hydrogen peroxide may react with thiocyanate in the following way:

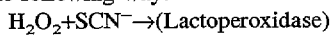
$H_2O_2$+$SCN^-$→(Lactoperoxidase)

$OSCN^-$, in which $OSCN^-$ is a bacteriostatic agent.

Gluten Strengthening

It is generally known that dough stability is one of the most important characteristics of a baking dough. Stable dough is important for both large scale and small scale applications. A strong dough will exhibit a greater tolerance of mixing time, of proofing time and of mechanical vibrations during dough transport, so that the baked product maintains its good quality. A weak dough will possess less tolerance. Therefore, a strong dough is generally preferred in most bread-making. A high gluten content and a good gluten quality form a stronger dough than a dough made from a low protein content or with poor gluten quality. In other words, a strong gluten network results in a strong dough, which has superior rheological and handling properties.

Dough "conditioners" to strengthen the gluten have long been used. The non-specific oxidants, such as bromate, ascorbic acid and peroxides have the gluten strengthening effect. It has been suggested that these conditioners induce the interprotein bonds which strengthen the gluten, thereby the dough. Enzymes used as dough conditioners are also known, e.g. glucose oxidase from *Aspergillus niger*.

The strengthening effect of a given dough conditioner on wheat flour dough or gluten dough may be measured by dynamic rheological measurements. These measurements are able to show the strength of a dough, under oscillation. Both wheat fluor dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ. An increase in the storage modulus G' and a decrease in the phase angle δ indicate a stronger and more elastic dough.

Baking industry/Additional Enzyme Activities

While the bread-improving composition or additive may comprise a glucose oxidase as the only enzyme added, the properties of dough and/or baked products may be further improved when the glucose oxidase is used in combination with one or more additional enzymes.

The additional enzyme(s) may either be one or more enzymes present in the glucose oxidase preparation recovered from the organism producing it, or may, more preferably, be added to the bread-improving composition or additive.

In a preferred embodiment, the additional enzyme is selected from the group consisting of an amylase, in particular an amyloglucosidase, an α-amylase or a maltogenic exo-amylase (at present contemplated useful for providing sugars fermentable by yeast), a peptidase, a maltogenase, a lipase, a cellulase, a hemicellulase, in particular a xylanase, a protease (at present contemplated useful for gluten weakening in particular when using hard wheat flour), and an oxidoreductase, e.g., a peroxidase, a laccase, a protein disulfide isomerase, e.g., a protein disulfide isomerase as disclosed in WO 95/00636, or an additional glucose oxidase.

In a more preferred embodiment, the additional enzyme is selected from the group consisting of a hemicellulase, in particular a xylanase, and an amylase, e.g., an amyloglucosidase, an α-amylase or a maltogenic exo-amylase.

The additional enzyme is preferably of microbial (bacterial, yeast or fungal) origin and may be obtained by techniques conventionally used in the art.

The amylase may be derived from a bacterium or a fungus, in particular from a strain of Aspergillus, preferably a strain of *Aspergillus niger* or *Aspergillus oryzae*, or from a strain of Bacillus. Commercially available α-amylases useful for the present purpose are Fungamyl™ (an *Aspergillus oryzae* α-amylase, available from Novo Nordisk A/S, Denmark), Novamyl™ (a *Bacillus stearothermophilus* maltogenic exo-amylase, available from Novo Nordisk A/S, Denmark), and BAN™ (a *Bacillus amyloliquefaciens* α-amylase, available from Novo Nordisk A/S, Denmark). The amyloglucosidase may in particular be AMG™ (an *A. niger* amyloglucosidase, available from Novo Nordisk A/S, Denmark). Other useful amylase products include Grindamyl™ A 1000 or A 5000 (available from Grindsted Products, Denmark) and Amylase™ H or Amylase™ P (available from Gist-Brocades, The Netherlands).

The additional glucose oxidase may be a fungal glucose oxidase, in particular Gluzyme™ (an *Aspergillus niger* glucose oxidase, available from Novo Nordisk A/S, Denmark).

The protease may in particular be Neutrase™ (available from Novo Nordisk A/S, Denmark).

The lipase may be derived from a strain of Thermomyces, a strain of Rhizomucor, a strain of Candida, a strain of Aspergillus, a strain of Rhizopus, or a strain of Pseudomonas. In particular the lipase may be derived from a strain of *Thermomyces lanuginosus*, a strain of *Rhizomucor miehei*, a strain of *Candida antarctica*, a strain of *Asgergillus niger*, or a strain of *Pseudomonas cepacia*. In specific embodiments, the lipase may be Lipase A or Lipase B derived from a strain of *Candida antarctica* as described in WO 88/02775, or the lipase may be derived from a strain of *Rhizomucor miehei* as described in EP 238,023, or a strain of *Humicola lanuginosa* described in EP 305,216, or a strain of *Pseudomonas cepacia* as described in EP 214,761 and WO 89/01032.

Besides the above mentioned additional enzymes, a microbial produced glucose oxidase preparation may contain varying minor amounts of other enzymatic activities inherently produced by the producer organism in question.

Detergent Compositions

According to the invention, the glucose oxidase may typically be a component (a hydrogen peroxide source) of a detergent composition, e.g., a laundry detergent composition or a dishwashing detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or amphoteric (zwitterionic). The detergent will usually contain 0–50% of anionic surfactant such as linear alkylbenzene-sulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid ethyl esters, alkyl- or alkenyl-succinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid onoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, cellulase, or peroxidase.

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may additionally contain other bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate.

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O, 2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as $Na_2SO4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, | 3–9% |
| or $C_{12-15}$ alcohol, 5 EO) | |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |

-continued

| | |
|---|---|
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O$, $2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3 \cdot 4H_2O$) | 0–20% |

-continued

| | |
|---|---|
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O$, $2SiO_2$) | 0–6% |
| Sodium citrate | 4–8% |
| Sodium percarbonate | 13–22% |
| TAED | 3–8% |
| Polymers (e.g. polycarboxylates and PVP) | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O$, $2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Particular forms of dishwashing detergent compositions within the scope of the invention include:

1) Powder Automatic Dishwashing Composition

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetylethylenediamine (TAED) | 1–4% |
| Sodium sulphate | 5–33% |
| Enzymes | 0.0001–0.1% |

2) Powder Automatic Dishwashing Composition

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetylethylenediamine (TAED) | 1–2% |
| Polyacrylate polymer (e.g. maleic acid/acrylic acid co-polymer) | 6–25% |
| Enzymes | 0.0001–0.1% |
| Perfume | 0.1–0.5% |
| Water | 5–10 |

3) Powder Automatic Dishwashing Composition

| | |
|---|---|
| Nonianic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly(amino acids) | 0–20% |
| Sodium polyacrylate | 0–8% |
| Enzymes | 0.0001–0.1% |

4) Powder Automatic Dishwashing Composition

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

5) Powder Automatic Dishwashing Composition

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes | 0.0001–0.1% |
| Sodium sulphate, water | Balance |

6) Powder and Liquid Dishwashing Composition with Cleaning Surfactant System

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes | 0.0001–0.1% |

7) Non-Aqueous Liquid Automatic Dishwashing Composition

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

8) Non-Aqueous Liquid Dishwashing Composition

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |

-continued

| | |
|---|---|
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

10) Liquid Automatic Dishwashing Composition

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetylethylenediamine (TAED) | 0–8% |
| Maleic acid/acrylic acid copolymer | 4–8% |
| Enzymes | 0.0001–0.1% |

11) Liquid Dishwashing Composition Containing Protected Bleach Particles

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature 369, 1994, pp. 637–639.

The glucose oxidase of the invention may be incorporated in concentrations conventionally employed in detergents. It is at present contemplated that, in the detergent composition of the invention, the glucose oxidase may be added in an amount corresponding to 0.00001–1 mg (calculated as pure enzyme protein) of glucose oxidase per liter of wash/dishwash liquor.

The present invention is further illustrated in the following examples which are not intended to be in any way limiting to the scope of the invention as claimed.

EXAMPLE 1

Glucose Oxidase from *Cladosporium oxysporum*

The glucose oxidase of the invention may be produced by the method described in this example.

Fermentation:

The glucose oxidase producing strain, e.g., *Cladosporium oxysporum*, CBS 163.94, was inoculated on agar plates containing a medium of the following composition:

| | |
|---|---|
| Yeast extract, Difco | 4 g/l |
| $K_2HPO_4$ | 1 g/l |
| $MgSO_4$ | 0.5 g/l |
| Glucose | 15 g/l |
| Distilled water | 1000 ml |
| Agar, Merck | 15 g/l |
| pH adjustment to 7.2. | |

Growth at 26° C. for 9 days.

The agar was cut into pieces and transferred aseptically to shake flasks, each flask containing 100 ml of inoculation medium of the following composition:

| | |
|---|---|
| Cornsteep liquor | 24 g/l |
| Glucose | 24 g/l |
| Water ad 1000 ml, pH adjustment to pH 5.5. | |
| soybeanoil | 0.5 ml/100 ml medium |
| $CaCO_3$ | 0.5 g/100 ml medium |

The flasks were incubated on a rotary shaker at 250 rpm, at 26° C., for 24 hours. The contents of these flasks were used for the inoculation of the production flasks which contained the following production medium (100 ml per flask):

| | |
|---|---|
| $NaNO_3$ | 3 g/l |
| $KH_2PO_4$ | 1 g/l |
| $MgSO_4, 7H_2O$ | 0.5 g/l |
| KCl | 0.5 g/l |
| $FeSO_4, 7H_2O$, 1% | 1 ml/l |
| Sucrose | 30 g/l |
| Yeast extract | 5 g/l |
| Distilled water | 1000 ml |
| Pluronic | 0.1 ml/l |
| pH adjustment to pH 6.4. | |

Growth at 26° C., 60 hours, 250 rpm.

Using the above described method a culture of *Cladosporium oxysporum*, CBS 163.94, gave a fermentation result of 5 UNITS/ml.

Purification and Characterization:

After separation of the solid material by centrifugation the glucose oxidase was filtrated and concentrated using a Filtron™ ultrafiltration module with a 10 kDa cut off membrane and filtrated again. The enzyme solution was then purified by hydrophobic interaction using the following conditions:

| | |
|---|---|
| Temperature: | 25° C. |
| pH: | 5.0 (adjusted with H₃PO₄) |
| Addition of salt: | 32.5% (w/w) (NH₄)₂SO₄ |
| Stirring: | 30 min. |
| Centrifugation: | Heraeus Sepatech Varifuge 20 RS 12000 × g; 30 min.; 25° C. (Precipitation discarded) |
| Resin: | Phenyl Sepharose CL-4B equilibrated with 30% (w/w) (NH₄)₂SO₄ |
| Addition of resin: | 1.0 g (dry sucked)/5.0 g supernatant |
| Stirring: | 30 min followed by dry suction |
| Wash of resin: | 30% (w/w) (NH₄)₂SO₄ 6–10 ml/g resin |
| Stirring: | 15 min. followed by dry suction |
| Elution: | Piperazine 20 mM pH 5.0 (HCl) 3–5 ml/g resin |
| Stirring: | 30 min. followed by dry suction |
| Elution: | Repeated as described above. |

After hydrophobic interaction purification the glucose oxidase solution was ultrafiltrated again, this time using a 20 kDa cut off membrane. Finally a ionexchange chromatography purification took place using a Pharmacia LKB HPLC/25° C. system using piperazine as buffer.

Yield: a supernatant of 2850 ml gave a final solution (after purification) of 30 ml, corresponding to approximately 53 mg glucose oxidase protein ($A_{200}$).

The MW and the pI of the glucose oxidase were estimated to 90–100 kDa (SDS-PAGE) and 4.1–4.3 (IEF) respectively. The found molecular weight (MW) may be that of a subunit (monomer).

pH Profile: The pH profile was performed using a glucose oxidase preparation which after fermentation as described above was ultrafiltrated using a 10 kDa cut off membrane and then precipitated with ethanol 55% (w/w) whereafter it was ultrafiltrated again resulting in a preparation with an activity of 200 UNITS/ml. The preparation was used to determine the pH profile previously described in this specification.

EXAMPLE 2

Glucose Oxidase from *C. oxysporum* for Gluten Strengthening

The dynamic shear storage modulus G' and the viscoelastic phase angle δ (defined as previously described) were measured in the gluten from 4 doughs, which were treated with different conditioners. The conditioners were added to the flour before dough mixing. The gluten was washed out of the flour dough containing the conditioner after the flour dough had been incubated at 32° C. for 1½ hours. The results of the tests are presented in FIGS. 2 and 3. The following symbols were used:

□: a dough with no added conditioner (=reference);

∇: a dough containing 20 ppm KBrO₃. KBrO₃ is a traditional dough conditioner;

◊: a dough containing 500 UNITS per kg of flour of a glucose oxidase from *A. niger;*

Figure 2:
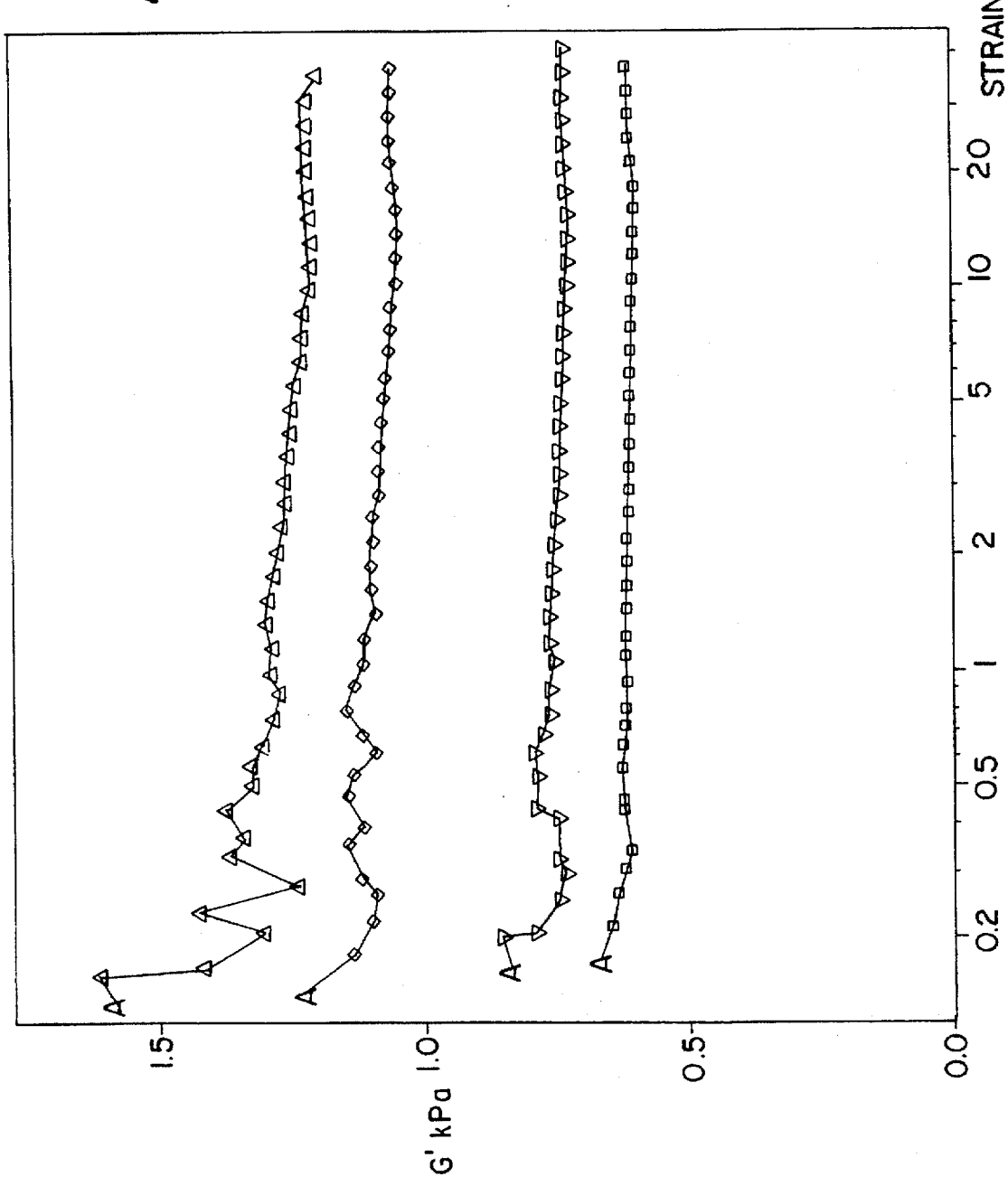
FIG. 2 shows the dynamic shear storage modulus G' in gluten from 4 different doughs characterized with the following symbols.

△: a dough containing 500 UNITS per kg of flour of a glucose oxidase of the invention, obtained as described in Example 1;

It can be seen from FIG. 2 that surprisingly the storage modulus G' of the gluten treated with the glucose oxidase of the invention is significantly higher than the G' of the gluten treated with the traditional glucose oxidase, dosed with the same amount of units, and also higher than the G' of the traditional dough conditioner KBrO₃. This result suggests that the gluten, thereby the dough, is significantly strengthened by addition of the glucose oxidase of the invention.

FIG. 3 shows that the traditional dough conditioner KBrO₃ as expected lowers the phase angle δ compared to the reference with no added conditioner; this indicates a more elastic rheological property. This decrease in phase angle is also found with the traditional glucose oxidase from *A. niger.* However, when using the glucose oxidase of the invention the phase angle δ is decreased even more when compared with the traditional conditioners.

The above demonstrated effects of the glucose oxidase of the invention can also be found when additionally glucose is added to the dough.

EXAMPLE 3

Baking Trial

Recipe (wheat flour pan bread):

| | |
|---|---|
| Wheat flour | 100% |
| Yeast | 2.5% |
| Salt | 2% |
| Sugar | 1% |
| Water | 54.5% |

Flour type: Flour without ascorbic acid (Intermill, Schweiz).

Preparation of bread, procedure:

1. Dough mixing (Spiral mixer)

3 min. at 700 RPM 6 min. at 1400 RPM the mixing time was determined and adjusted by a skilled baker so as to obtain an optimum dough consistence under the testing conditions used.

2. Fermentation 28° C.—60% RH, 40 min.
3. Sheeting, moulding and panning.
4. Fermentation 32° C.—80% RH, 70 min.
5. Baking: 230° C., 35 min.

Evaluation of Dough and Baked Bread

Dough and baked breads described in this example were evaluated as follows:

Loaf specific volume: The mean value of 4 loaves volume were measured using the traditional rape seed method. The specific volume was calculated as volume ml per g bread. The specific volume of the control (without enzyme) was defined as 100. The relative specific volume index was calculated as:

$$\text{Specific vol. index} = \frac{\text{specific vol. of 4 loaves}}{\text{spec. vol. of 4 control loaves}} * 100$$

The dough stickiness, firmness, extensibility, elasticity and flavour as well as the colour/crust crispy/crumb structure of the breads were evaluated according to the following score system:

| | | |
|---|---|---|
| Dough Stickiness: | almost liquid | 1 |
| | too sticky | 2 |
| | sticky | 3 |
| | normal | 4 |
| | dry | 5 |
| Dough Firmness: | very soft | 1 |
| | too soft | 2 |
| | soft/good | 3 |
| | normal | 4 |
| | firm | 5 |
| | too firm | 6 |
| Dough Extensibility: | very short | 1 |
| | short | 2 |
| | normal | 3 |

|  |  |  |
|---|---|---|
| Dough Elasticity: | good | 4 |
|  | long | 5 |
|  | too long | 6 |
|  | very strong | 1 |
|  | strong | 2 |
|  | normal | 3 |
|  | good | 4 |
|  | weak | 5 |
|  | too weak | 6 |
| Dough Flavour: | less | 2 |
|  | normal | 3 |
|  | good | 4 |
| Bread Colour: | very light | 1 |
|  | light | 2 |
|  | normal | 3 |
|  | good | 4 |
|  | very good | 5 |
|  | too dark | 6 |
| Crust Crispy: | too rubbery | 1 |
|  | rubbery | 2 |
|  | normal | 3 |
|  | good/crispy | 4 |
|  | very good | 5 |
|  | too crispy | 6 |
| Crumb Structure: | very poor | 1 |
|  | poor | 2 |
|  | non-uniform | 3 |
|  | uniform/good | 4 |
|  | very good | 5 |

Shock test: After the second fermentation the breads were exposed to an over fermentation of 10 min, 32° C., 80% RH, (i.e. for these breads the second fermentation lasted 80 min. in all), whereafter a pan containing the dough was dropped from a height of 20 cm. The dough was then baked (225° C., 30 min.) and the volume of the resulting bread was determined.

TABLE 1

| Evaluation Doughs | | | |
|---|---|---|---|
| Glucose Oxidase UNITS/kg flour | 0 | 250 | 500 |
| Stickiness | 4 | 4.5 | 5 |

TABLE 1-continued

| Evaluation Doughs | | | |
|---|---|---|---|
| Firmness | 4 | 4.5 | 5 |
| Extensibility | 3 | 2.5 | 2 |
| Elasticity | 3 | 3 | 3 |
| Flavour | 3 | 3 | 3 |

It can be seen from Table 1 that glucose oxidase showed good effects on dough consistency such as decreased stickiness and improved firmness thereby strengthening the gluten net and thereby improving the stability.

TABLE 2

| Evaluation Breads. | | | |
|---|---|---|---|
| Glucose Oxidase UNITS/kg flour | 0 | 250 | 500 |
| Specific volume index % | 100 | 110 | 120 |
| Colour | 3 | 4 | 5 |
| Crust crispy | 3 | 4 | 5 |
| Crumb structure | 3 | 4 | 2.5 |
| After shock test Specific volume index % | 100 | 117 | 136 |

It can be seen from Table 2 that glucose oxidase of the invention has a significant effect on improving the baking quality of flour. The specific volume increased between 10% to 20%, and the breads also performed very well after shock test. The colour, the crust crispy and the crumb structure were also improved after adding glucose oxidase, only the crumb structure did not perform so satisfactory if the glucose oxidase is dosed higher than 400–500 UNITS per kg flour.

We claim:

1. An isolated glucose oxidase having a pH optimum in the range pH 6–7, determined at 30° C. with D-glucose as substrate, having more than 75% of maximum activity at pH 8, determined at 30° C. with D-glucose as substrate, and is obtained from a strain of *Cladosporium oxysporum*, designated as CBS 163.94.

2. A dough conditioner composition comprising the glucose oxidase of claim 1.

3. A pre-mix for baked products which comprise the glucose oxidase of claim 1.

4. A method for producing the glucose oxidase of claim 1 comprising culturing a cell transformed with a DNA construct comprising a DNA sequence encoding said glucose oxidase under conditions conducive to the production of the glucose oxidase and subsequently recovering the glucose oxidase from the culture.

* * * * *